United States Patent
Hansen et al.

(10) Patent No.: US 6,663,861 B2
(45) Date of Patent: Dec. 16, 2003

(54) METHOD OF PRODUCING ANTIBODIES BY IMMUNIZATION WITH CONJUGATES OF MOLECULES COUPLED TO CHARGE-MODIFIED PROTEINS

(75) Inventors: Trine Overgaard Hansen, Copenhagen-East (DK); Camilla Recke, Kongens Lyngby (DK)

(73) Assignee: AntibodyShop A/S, Copenhagen S (DK)

( * ) Notice: Subject to any disclaimer, the term of this patent is extended or adjusted under 35 U.S.C. 154(b) by 0 days.

(21) Appl. No.: 10/037,080

(22) Filed: Nov. 9, 2001

(65) Prior Publication Data

US 2002/0081631 A1 Jun. 27, 2002

Related U.S. Application Data

(60) Provisional application No. 60/247,429, filed on Nov. 9, 2000.

(51) Int. Cl.$^7$ ...................... A61K 39/395; A61K 39/00; A61K 39/38
(52) U.S. Cl. ................ 424/130.1; 424/179.1; 424/193.1; 424/194.1
(58) Field of Search ........................ 424/130.1, 193.1, 424/179.1, 194.1

(56) References Cited

U.S. PATENT DOCUMENTS

| | | | |
|---|---|---|---|
| 5,585,103 A | 12/1996 | Raychaudhuri | 424/278.1 |
| 5,955,077 A | 9/1999 | Andersen et al. | 424/184.1 |
| 6,017,513 A | 1/2000 | Betbeder et al. | 424/1.73 |

FOREIGN PATENT DOCUMENTS

| | | |
|---|---|---|
| EP | 0 329 185 A2 | 2/1989 |
| EP | 0 783 892 A1 | 7/1997 |
| WO | WO 89/06974 | 8/1989 |
| WO | WO 94/12213 | 6/1994 |

OTHER PUBLICATIONS

Bradford M.M., "A Rapid and Sensitive Method for the Quantitation of Microgram Quantities of Protein Utilizing the Principle of Protein–Dye Binding", Analytical Biochemistry 1976 72:248–254.
Erlanger B.F., "[4] The Preparation of Antigenic Hapten–Carrier Conjugates:A Survey", Methods in Enzymology 1980 70:85–104.
Griffin et al., "Initial Clinical Study of Indium–111–Labeled Clone 110 Anticarcinoembryonic Antigen Antibody in Patients With Colorectal Cancer", J. of Clinical Oncology 1991 9 (4) :631–640.
Jean J., "Production and characterization of polyclonal antibodies against cholecalciferol (vitamin D3)", J. Immunological Methods 1999 223:155–163.
Landsteiner K., "The Specificity of Serological Reactions", Harvard University Press, Cambridge, Massachusetts 1945 157–211.
Lauffer R.B., "Targeted Relaxation Enhancement Agents for MRI*", Magnetic Resonance in Medicine 1991 22:339–342.
Lussow et al., "Use of tuberculin purified protein derivative–Asn–Ala–Asn– Pro conjugate in bacillus Calmette–Guérin primed mice overcomes H–2 restriction of the antibody response and avoids the need for adjuvants", Proc. Natl. Acad. Sci. USA 1990 87:2960–2964.
Mitchison N.A., "The carrier effect in the secondary response to hapten–protein conjugates. I. Measurement of the effect with transferred cells and objections to the local environment hypothesis", Eur. J. Immunol. 1971 1:10–17.
Mitchison N.A., "The carrier effect in the secondary response to hapten–protein conjugates. II. Cellular cooperation", Eur. J. Immunol. 1971 1:18–27.
Rajewsky et al., "The Requirement of More Than One Antigenic Determinant for Immungenicity", J. Exp. Med. 1969 129:1131–1143.
Stryer Lubert Biochemistry—4th Edition, Freeman and Co., New York 1995 p. 379.
Tsumuraya et al., "Catalytic Antibodies Induced by a Zwitterionic Hapten", Chem. Eur. J. 2001 7(17):3748–3755.
Ferro V. et al., "Immunological castration using a gonadotrophin–releasing hormone analogue conjugated to PPD", Database Accession No. PREV199598553492 XP002902634, 1995.
Morrison C.A. et al., "Adjuvant–free immunological manipulationof livestock", Database Accession No. NLM6147886 XP002902635, 1984.

Primary Examiner—Christina Chan
Assistant Examiner—Michail Belyavskyi
(74) Attorney, Agent, or Firm—Licata & Tyrrell P.C.

(57) ABSTRACT

A method for raising antibodies against molecules, particularly molecules with low immunogenicity, by coupling the molecule to a carrier containing a balanced charge mixture of proteins is provided. Also provided are antibodies and immunoassays containing antibodies raised in accordance with these methods. Pharmaceutical compositions containing these antibodies or a part thereof and methods of using these compositions to treat various diseases and infections are also provided. In addition, vaccines containing an antibody or an immunogenically stimulatory amount of a molecule coupled to the carrier of a balanced charge mixture of proteins and methods of inducing an immune response in an animal against the molecule by administration of these vaccines are provided.

3 Claims, No Drawings

METHOD OF PRODUCING ANTIBODIES BY IMMUNIZATION WITH CONJUGATES OF MOLECULES COUPLED TO CHARGE-MODIFIED PROTEINS

This application claims the benefit of priority from U.S. Provisional Application Ser. No. 60/247,429, filed Nov. 9, 2000.

FIELD OF THE INVENTION

The present invention relates to antibodies against molecules, particularly haptens and other B cell antigens, and methods for their preparation. In the methods of the present invention, the molecule is conjugated to a carrier comprising a mixture of charge-modified proteins prior to raising of the antibodies in a host animal. The host animal is pre-immunized with unmodified proteins of the carrier. The host animal is then immunized with the molecule complexed with the carrier wherein proteins in the mixture making up the carrier have been charge-modified. Antibodies or B cells producing antibodies can then be routinely isolated from the host animal. The present invention also relates to methods for use of these antibodies in immunoassays as well as in therapeutic applications. In addition, the present invention relates to vaccine therapies and methods of invoking and/or enhancing an immune response in animals via molecules coupled to carriers comprising a mixture of charge-modified proteins.

BACKGROUND OF THE INVENTION

The general humoral immune response is based on the cooperation of antigen presenting cells, antigen specific T lymphocytes and antigen specific B lymphocytes.

T lymphocytes are selected and stimulated by T cell epitopes, which associate with Major Histocompatibility Complex (MHC) and are presented on the surface of antigen presenting cells. A T cell epitope is a short, linear amino acid sequence most frequently localized to the interior portion of a protein and thus inaccessible from the protein surface. A T cell epitope reacts with the antigen specific receptor of the T cell only when bound to an MHC molecule thus forming part of a ternary complex. Helper T cells participate in determining what kinds of immunoglobulins are produced by B cells and stimulate the proliferation of specified lymphocytes. Peptides arising from the digestion of internalized and endocytosed proteins by a B cell are bound to MHC proteins and stimulate and activate helper T cells.

Accordingly, these T cell epitopes react with the antigen specific receptor of the helper T cell only when the helper T cell epitope is bound to an MHC Class II molecule.

B lymphocytes are selected by antigens which bind to the antigen specific receptor (a membrane bound antibody) of the B cell. Almost any molecular configuration can act as a B cell antigen or B cell epitope. With respect to proteins, the epitopes are most frequently positioned on the outer accessible face of the protein as direct binding to the antigen specific receptor is required. The T cell epitope of the antigen is then presented on the surface of the B cell, associated with MHC class II molecules. MHC class II proteins, which comprise the T cell epitopes, arise from the degradation of proteins that have been internalized. This presentation entails the selected and stimulated T accessory cells to be associated with the antigen specific B lymphocyte, which is now stimulated and matured via hormone like factors from the T cell. The final stage of the B cell after stimulation and maturing is the antibody producing plasma cell, which secretes antigen specific antibody (Biochemistry ed. Lubert Stryer 4th Edition, Freeman and Co., New York pp. 379).

Thus, antibody formation against an antigen is conditional upon the presence of both B cell epitopes and T cell epitopes. Further, it has been demonstrated that the two types of epitopes must be physically associated to generate an antibody immune response (Rajewsky et al. *J. Exp. Med.* 1969 129:1131; Mitchison, N. A. Eur. J. Immunol. 1971 1:10; and Mitchison, N. A. Eur. J. Immunol. 1971 1:18).

Accordingly, the antibody response to low molecular weight molecules such as haptens is often quite poor and can be induced in a mammal only by presentation of the low molecular weight molecule coupled to an immunogenic carrier. Coupling to an immunogenic carrier is also required for relatively large molecular weight molecules with only limited immunogenicity such as larger peptides, low immunogenic proteins (such as self-proteins), carbohydrates, lipids, viruses and nucleic acids. Coupling to an immunogenic carrier also provides a means for enhancing the immunogenicity of immunogenic proteins wherein a more powerful immunogenicity is required. Some examples of carrier molecules which have been disclosed for inducing or enhancing an immune response to such molecules include serum albumin such as bovine serum albumin (BSA), human serum albumin (HSA) and others, keyhole limpet hemocyanin (KLH), ovalbumin (OA), chicken immunoglobulin (IgY) and diphtheria toxoid.

Conjugation methods have also been described for increasing the immunogenicity of low molecular weight molecules. Pioneering work to enhance the immunochemistry of low molecular weight molecules began as early as 1917 when antigens were covalently conjugated by azo reaction on histidine, tyrosine and tryptophan residues (Landsteiner, K. The Specificity of Serological Reactions" Harvard Univ. Press, Cambridge, Mass., 1945). More recently, methods have been described for preparing hapten-carrier conjugates via formation of covalent bonds between the low molecular weight hapten and a carrier protein selected from a wide range of globulin fractions (Erlanger, B. F. The Preparation of Antigenic Hapten-Carrier Conjugates: A Survey" in Methods of Enzymology, 70, Academic Press, Inc. 1980). In these methods, the functional groups of the hapten determine which synthesis is selected for conjugation of the functional groups of the carrier to the antigen. A wide range of chemical syntheses have been described for conjugating hapten on the basis of hapten functionality.

In addition to invoking an antibody response, it is also desirable to avoid antigen-specific suppression wherein prior immunity against a carrier protein reduces the response to re-inoculation with the same carrier protein coupled to an antigen. This effect can be avoided or reduced, enabling expansion of native B cell populations, if the carrier molecules, for example secretory proteins from BCG, are sufficiently modified at the surface. Reduction of B cell response to the carrier molecule can be achieved by chemical or physical modification of the carrier molecule. Examples of chemical and/or physical processes, which have been described for modification of the carrier molecule include heat denaturation and chemical methylation or formaldehyde treatment of the carrier molecule prior to the coupling to the hapten molecule.

Modification of the carrier to avoid epitope-specific suppression has several additional advantages. Specifically, since T cell immunity can be induced as a general principal in animals, the T cell immunity can be retrained against the modified carrier while considerably reducing the degree of B cell immunity against the carrier molecule.

Accordingly, subsequent immunization with a B cell antigen coupled to a modified form of the carrier ensures a rapid development of antibodies, a high level of antibodies after only one or two immunizations, a sustained immune response, and the possibility of rapid development of antibodies having a high binding strength.

WO 94/12213 describes a process for modifying an immunogenic protein to be exclusively or predominantly a T cell antigen by blocking charged groups, either —$NH_3^+$ or —$COO^-$. —$NH_3^+$ groups are blocked by means of formaldehyde, while disulfide bridges are reduced by means of dithiothreitol or β-mercaptoethanol. Denaturation of the protein antigen is then performed by heat treatment.

The present invention relates to a new method for raising antibodies against molecules with low antigenicity by conjugating the molecule to a carrier comprising a balanced charge mixture of proteins chemically modified to carry a net positive or negative charge.

SUMMARY OF THE INVENTION

An object of the present invention is to provide a method for raising antibodies against molecules including, but not limited to, those with low immunogenicity. The method comprises coupling the molecule to a carrier comprising a balanced charge mixture of proteins, each protein of the mixture being chemically modified to carry either a net positive or negative charge. In this method a host animal is pre-immunized with unmodified proteins of the carrier or the host attenuated bacteria or virus from which the carrier proteins are derived. The host animal is then immunized with the molecule coupled to a carrier comprising a balanced charge mixture of the proteins, each protein of the mixture being chemically modified to carry either a net positive or negative charge. Antibodies raised against the molecule by the host animal can then be isolated in accordance with well known methods.

Another object of the present invention is to provide antibodies raised in accordance with this method.

Another object of the present invention is to provide immunoassays and immunoassay kits, which use antibodies raised in accordance with this method.

Another object is to provide pharmaceutical compositions comprising antibodies raised in accordance with this method, as well as methods of using these pharmaceutical compositions in therapeutic applications.

Yet another object of the present invention is to provide vaccines and methods of inducing an immune response in animals by administering vaccines comprising either an antibody raised in accordance with the method of the present invention or a molecule coupled to a carrier comprising a balanced charge mixture of proteins, each protein of the mixture being chemically modified to carry either a net positive or negative charge.

DETAILED DESCRIPTION OF THE INVENTION

The present invention relates to a complex carrier system for generating antibodies. In this system, the carrier molecule is modified by chemical treatment, preferably via formaldehyde treatment and acylation of a protein mixture, to make the product carry a net positive or negative charge. Accordingly, in this technique, the protein mixture is denatured by treatment that removes a particular group that is necessary to form a hydrogen bond with another group on the protein. A second batch of protein is also prepared with the other group modified. Through subsequent combination of the two different groups, equalization of the opposite charges is achieved and a charge balance is obtained. This process results in the production of an electrically neutral carrier molecule complex with pertinent advantages for fulfillment of the objective of raising specific antibodies in an efficient manner. Specifically, the carrier molecule complex retains the identity characteristics of the original component proteins while constituting a conjugate that has increased greatly in size and complexity.

For purposes of the present invention, the carrier molecule to be modified is an immunogenic protein. For example, the carrier molecule may comprise protein molecules such as serum albumin, e.g., BSA (bovine serum albumin) and HSA (serum albumin), OA (ovalbumin) or mixtures thereof, e.g. BSA (positive charge) and OA (negative charge). Suitable immunogenic proteins for carrier molecules can also be derived from intracellular bacteria including, but not limited to, Salmonella sp., Ricketsia, Chlamydia, Brucella, *Mycobacter tuberculosis, Mycobacter leprae, Listeria monocytogenes, Leishmania donovni, Plasmodium vivax* and *Franasella tularensis.* Suitable materials for carrier molecules can also be derived from organisms such as viruses. Examples of various immunogenic proteins for use in the present invention are also described in U.S. Pat. No. 5,955,077, WO 94/12213 and WO 89/06974.

A preferred protein mixture useful in the present invention is the SP (secretory protein) from intracellular bacteria. In this embodiment, a crude filtrate from intracellular bacteria is divided into two portions, the first portion being treated with formaldehyde to produce a portion carrying a net negative charge, the second portion being esterified by acylation to produce a portion carrying a net positive charge. In a preferred embodiment of the present invention, the SP carrier compound used for the preparation of antibodies is derived from Bacille Calmette-Guerin (BCG) However, as will be obvious to those of skill in the art upon this disclosure other carrier compounds can also be used.

There are several advantages in using a carrier complex of mixed SP products from Bacille Calmette-Guerin (BCG) after treatment by esterification or with formaldehyde to raise antibodies against a molecule with low immunogenicity. Specifically, particulate, or sparingly soluble complexes are formed between the positively charged esterified, methylated protein solution and the negatively charged formaldehyde treated solution. These complexes are more immunogenic than the individual soluble carrier protein materials. In addition, there is an adjuvant effect related to the non-covalent binding nature of the bonding of the complexes formed by combining the positively and negatively charged proteins. This bonding results in slow release of the single molecule-carrier conjugates which is similar to that obtained with $Al(OH)_3$ adjuvant. The ability to adjust and control the charge balance by changing the relative proportions of the positive and negative charged SP portions also enables optimization of the immunogenic effect. Further, because of the increased size of the complexes from non-specific coupling, the ability of antigen presenting cells to take up the complexes and transport them to the local lymph node is enhanced.

As will be obvious to those of skill in the art upon this disclosure, other methods for obtaining positive charged and negative charged proteins fractions can also be used. Other methods of obtaining positive and negative charged proteins are described, for example, by Erlanger, B. F. (The Preparation of Antigenic Hapten-Carrier Conjugates: A Survey" in Methods of Enzymology, 70, Academic Press, Inc. 1980) and WO 94/12213.

The coupling of a molecule with low antigenicity to a carrier to form a complex comprising the coupled molecule and carrier can be performed either covalently or non-covalently. Coupling of a hapten or B cell antigen can be achieved by mixing the positively charged protein mixture with the negatively charged protein mixture and with the hapten. Simple mixing of these compounds results in formation of non-covalent bonds between the molecules.

Alternatively, the hapten can be covalently coupled to either the positive or negative protein mixtures before combining the protein mixtures. Various methods for covalent coupling are known and selection of the method is based upon the molecule being coupled to the carrier. For example, coupling of a molecule with sulfhydryl groups can be performed by homobifunctional coupling with the 1,4-bis-maleimidobutane (BMB) reagent. Coupling of a carbohydrate molecule can be performed using sodium periodate. Coupling of a molecule with carboxyls can be performed using 1-ethyl-3-(3-dimethylaminopropyl) carboiimide hydrochloride. Coupling of a molecule with hydroxyls to sulfhydryls can be performed using N-(p-maleimidophenyl) isocyanate. Alternatively, non-selective/photoreactive coupling can be performed using N-5-azido-2-nitrobenzoyloxysuccinimide. Covalent coupling of a molecule to the carrier can also be achieved via glutaraldehyde coupling.

Glutaraldehyde is a dialdehyde homobifunctional cross-linker that provides covalent bonds to amino-groups on both hapten and carrier proteins. The reaction between one end of the dialdehyde glutaraldehyde and a primary amine is termed as nucleophilic addition-elimination resulting in the formation of an imine group thus binding the glutaraldehyde. Specific methods for glutaraldehyde coupling a hapten to a carrier protein of the present invention are set forth in Example 5.

In yet another embodiment the molecule is coupled to the carrier to form the complex comprising the molecule coupled to the carrier after the two protein mixtures are combined.

One advantage in conjugating carriers of both positive and negative charged proteins to molecules with low antigenicity is the effect upon immunization as the large complexes are engulfed by macrophages and other antigen presenting cells. Further, T cell epitopes are not destroyed by the chemical modifications. In addition, the modified carriers of the present invention have an activating effect on the immune response as the reformed hydrogen bridges between —$NH_2$ nuclei and COOH allow for formation of large complexes which are engulfed and transported to the lymph nodes more readily by macrophages and other antigen-presenting cells. Macrophages and other antigen presenting cells which engulf the complex recognize features of the complex that are unknown or not previously presented, i.e. the complexed hapten. However, the similarities of the antigenic features of the carrier with the pre-immunization antigen are also recognized. T cell epitopes on the complex are not destroyed or modified by chemical treatment and their high levels results in somatic hypermutation thereby resulting in antibodies with much higher affinity.

Once formed, the complex is administered to a host animal so that antibodies are produced against the molecule and/or B cells producing antibodies against the molecule are produced. Antibodies can be isolated from these host animals in accordance with well known techniques. B cells can also be isolated and used to produce hybridomas in accordance with well known techniques.

Pre-immunization of the host animal with proteins used in the complex of the present invention is required. However, in this pre-immunization step the charge of proteins is not modified. These proteins are referred to herein as "unmodified proteins". By "unmodified proteins" it is meant to include not only the proteins used in the carrier but also the entire intracellular bacteria or virus or attenuated bacteria or viruses from which the charge modified proteins of the carrier are derived. In a preferred embodiment, the unmodified proteins used in the pre-immunization step comprise the entire intracellular bacteria or virus or attenuated bacteria or virus. The advantages of pre-immunization with the protein or proteins followed by immunization with the complex containing modified proteins of the present invention are that pre-immunization generates a high incidence of specific T cells. See e.g. U.S. Pat. No. 5,955,055. Because the immune response is a T cell response there will be a high degree of somatic hypermutation in comparison with methods with no pre-immunization step. Examples of host animals used to produce antibodies include, but are not limited to, rodents, lagomorphs, equines, bovines, ovines, canines, felines, porcines and the like.

In a preferred embodiment, the antibodies of the present invention are human or humanized. Various methods for producing humanized antibodies have been described. In one embodiment, antibodies can produced against the carrier coupled molecule in animals genetically modified to produce humanized antibodies. Transgenic mice for production of humanized antibodies are known in the art. Antibodies can be isolated from these host animals in accordance with well known techniques.

In another embodiment, humanization is performed via reshaping or complementarity determining region (CDR) grafting. These techniques for humanization are well-established and reduce the immunogenicity of monoclonal antibodies from other animal species in humans. These techniques can be used to humanize antibodies produced from existing animal antibody-producing cell lines such as mouse antibody-producing cell lines. In CDR grafting, the antigen-binding region of a mouse antibody, for example, is genetically engineered onto the immunoglobulin framework of a human antibody. More specifically, genes encoding the antigen binding regions (CDRs) of the mouse antibody are isolated and merged with the genes encoding a normal human antibody. The result is a human antibody with mouse antigen binding regions. This technique offers a means for introducing a novel antibody into a human while bypassing the normal anti-idiotypic immune response to introduction of a foreign protein.

Humanization of antibodies of the present invention can also be obtained via phage display or from human monoclonal clones in accordance with well known techniques.

The carriers of the present invention are particularly useful in inducing an antibody response against molecules with low antigenicity. Examples of molecules with low antigenicity include, but are not limited to, low molecular weight haptens and higher molecular weight molecules with low antigenicity such as larger peptides, low immunogenic proteins, carbohydrates, lipids and nucleic acids. Examples of haptens or low molecular weight molecules against which antibodies can be raised in accordance with the method of the present invention include, but are in no way limited to, 2,6 dichlorobenzamide, triazines and other pesticides, anti-malarial drugs as well as other low molecular weight drugs, and steroid hormones. Examples of proteins with low immunogenicity against which antibodies can be raised in accordance with the method of the present invention include, but are in no way limited to, interleukins, immunoglobulins, cell markers, albumins, peptide hormones, and prions. Examples of carbohydrates against which antibodies can be raised in accordance with the method of the present invention include, but are in no way limited to, glycogen, cellulose, glucose, maltose, lactose and cellobiose. Examples of lipids against which antibodies can be raised in accordance with the method of the present invention include, but are in no way limited to, lipopolysaccharides, triglycerols, lipid membranes, phospholipids, liposomes, and fatty acids.

However, as will be understood by those of skill in the art upon reading this disclosure, the method of the present invention can also be used to enhance immunogenicity of highly immunogenic proteins. Examples of highly immunogenic proteins against which antibodies can be raised in accordance with the method of the present invention include, but are in no way limited to, bacterial and viral proteins, surface proteins of non-self cancer cells, plant proteins, gluten, milk proteins, and bacterial exotoxins. Antibodies can be raised against proteins of bacteria including, but certainly not limited to, Streptococci, *Staphylococcus aureus, E. coli,* Pneumococci, Salmonella, and Borellia, and viruses including, but certainly not limited to, cytomegalovirus, Epstein Barr Virus, HIV, Influenza, and Hepatitis.

Using the method and carrier system of the present invention, antibodies were raised against the hapten, chloroquine. Chloroquine is a common anti-malarial drug sold over the counter in many countries. Due to its widespread availability, an increase in both unintentional intoxications and attempted suicides with this compound has occurred. The toxic effects of chloroquine are blurred vision, vertigo, tinnitus, nausea, shock, convulsions, coma, heart arrhythmias, and respiratory inhibition. In cases of overdose, gastric lavage is performed as well as treatment with the vasoconstrictor diazepam and sometimes assisted ventilation. Ineffective compliance and use of subtherapeutic doses of chloroquine actually increases the risk for contracting malaria. In fact, inefficient use of chloroquine in malarious areas has been suggested to provoke the appearance of chloroquine resistant *P. faliparum.* Thus, the ability to monitor chloroquine levels in non-infected and infected patients would be useful, especially in children and patients with malabsorption and gastrointestinal disorders. Several calorimetric field methods for measuring chloroquine levels are available. The Dill-Glazko test was used widely until recent reports of unreliability. Other field methods include the Saker-Solomon, the Haskins and the Bromothymol Blue method. While these tests perform better than the Dill-Glazko test, they still lack sensitivity and specificity. The most reliable method for chloroquine detection is via HPLC. However, HPLC methods are time consuming, labor intensive and can only be performed in well-equipped laboratories. Accordingly, there is a need for a low cost, reliable and quick field method of chloroquine measurement which is satisfied with antibodies raised against chloroquine using the systems and methods of the present invention.

Using the method of the present invention, antibodies against chloroquine were raised against the side chain to the quinoline moiety of chloroquine, 2-amino-5-diethylaminopentane (ADP). ADP contains a primary amine which is reactive in glutaraldehyde coupling reactions. Further, this is the portion of the chloroquine molecules which antibodies preferably recognize in order to avoid cross reactivity towards metabolites of chloroquine and other malarial drugs.

A detailed protocol of experiments in mice administered the ADP antigen is provided in Example 7. The experiments demonstrated that mice (n=5) administered ADP in combination with SP +/− in accordance with the method of the present invention exhibited higher antibody production as early as the second bleed as compared to mice administered ADP and SP which was not charge modified. Further, comparison of the antibody titer between the first and second bleed in each group showed mice treated with ADP in combination with +/− SP to exhibit an 8.4-fold increase in antibody titer while mice receiving ADP in combination with SP which was not charge modified exhibited only a 4.9-fold increase in antibody titer.

Antibodies raised against a molecule in accordance with the method of the present invention can be incorporated into immunoassay kits for detection of the molecule. The immunoassay kits of the present invention comprise these antibodies. In a preferred embodiment, the antibodies are detectably labeled. Examples of detectable labels include, but are not limited to, enzymes, fluorophores and radiolabels. Immunoassay kits of the present invention may further comprise detection means for the labeled antibodies, standards, and dilution and/or washing buffers.

Antibodies raised in accordance with the method of the present invention and isolated from a host animal can also be used in vivo as diagnostic imaging agents and incorporated into pharmaceutical compositions for protection against and treatment of various infections and diseases. The use of antibodies for in vivo diagnosis and treatment is well known in the art. For example, antibody-chelators labeled with Indium-111 have been described for use in the radioimmunoscintographic imaging of carcinoembryonic antigen expressing tumors (Sumerdon et al. Nucl. Med. Biol. 1990 17:247–254). In particular, these antibody-chelators have been used in detecting tumors in patients suspected of having recurrent colorectal cancer (Griffin et al. J. Clin. Onc. 1991 9:631–640). Antibodies with paramagnetic ions as labels for use in magnetic resonance imaging have also been described (Lauffer, R. B. Magnetic Resonance in Medicine 1991 22:339–342). Antibodies raised in accordance with the method of the present invention can be used in a similar manner.

In this embodiment, it is preferred that the host animal from which the antibodies are derived be transgenically modified to produce antibodies compatible with the target animal. Alternatively, following production the antibody can subsequently be modified for compatibility with the target animal.

Pharmaceutical compositions comprising an antibody or a part thereof produced in accordance with the method of the present invention can be formulated in accordance with well known techniques. Parts of antibodies preferred for use in the present invention include, but are not limited to Fab fragments and Fv fragments. Pharmaceutically acceptable vehicles for formulation of compositions comprising an antibody are well known and can be selected routinely by one of skill in the art based upon the selected route of administration for the pharmaceutical composition. For example, for intravenous administration, pharmaceutical compositions of the present invention will preferably comprise an antibody produced in accordance with the method of the present invention in a pharmaceutically acceptable vehicle such as phosphate buffered saline.

Pharmaceutical compositions comprising an antibody or part of an antibody produced in accordance with the method of the present invention can be administered to a subject in need thereof in accordance with well known procedures to treat various diseases and/or infections.

In addition, carriers of the present invention coupled to a selected molecule can be used as vaccines to invoke an immune response against the selected molecule. These vaccines comprise an immunogenically stimulatory amount of the carrier coupled to the selected molecule. Immunogenically stimulatory amount refers to that amount of carrier coupled molecule that is able to invoke the desired immune response in the recipient for the protection against, amelioration, or treatment of the disease for which the vaccine is being administered. Effective amounts may be determined empirically by standard procedures well known to those skilled in the art. In this embodiment, the vaccine therapy further comprises a pre-immunization step wherein the recipient is administered unmodified proteins of the carrier prior to immunization with the molecule coupled to the carrier of proteins which have been chemically modified to carry either a net positive or negative charge.

The antibody or carrier coupled molecule may be provided in any one of a number of vaccine formulations which are designed to induce the immune response. Such formulations are known in the art and include, but are not limited to, formulations such as those described in U.S. Pat. No. 5,585,103. Vaccine formulations of the present invention used to stimulate immune responses can also include pharmaceutically acceptable adjuvants such as $Al(OH)_3$.

The following nonlimiting examples are provided to further illustrate the present invention.

EXAMPLES

Example 1
Protein Production Protocol (SP)

SP is produced from the rinse-water of a culture of BCG cells used for vaccine production and is used for immunization after pre-immunization with live BCG-vaccine intraperitoneally. The third supernatant rinse arising in the production of BCG vaccine is filtered first through a 1.2 $\mu$m filter and thereafter through a 0.22 $\mu$m filter. The filtered product is concentrated on Millipore Easy-Load Masterflex with a Prep/Scale TM-TFF 2.5 ft$^2$ cartridge filter. The protein concentration is determined with the Bradford-method (Bradford, M. M. Analytical Biochemistry 1976 72:248–254). Bovine Serum Albumin (BSA) is used as the standard and Purified Protein Derivative (PPD) is used as the reference protein.

Example 2
Positively Charged Complexes

SP from Bacille Calmette-Guerin (BCG) are acylated to obtain a positively charged protein mixture by the method of Fraenkel-Conrat and Alcott. In this method, the carboxyl groups on the polypeptide chains are esterified by alcohol at a suitable pH. Protein (10 mg) is suspended in 1 ml methanol. HCl (8.4 $\mu$l 12 N) is added so that the protein dissolves and then eventually precipitates again. The mixture is allowed to stand in the dark for 3 days rotating end over end. The mixture is centrifuged and the precipitate is washed three times in methanol. The precipitate is frozen at −80° C. and lyophilized. The methylated protein is water soluble

Example 3
Negatively Charged Complexes

SP from Bacille Calmette-Guerin (BCG) are treated with formaldehyde in order to obtain a negatively charged protein mixture. In this procedure, the protein concentration is first adjusted to 3 g/l in 0.1 M phosphate buffer. Formaldehyde is added to a final concentration of 0.025 M. L-lysine is then added to a final concentration of 0.025 M. The samples are then sterilized. Following sterilization, the samples are mixed at 37° C. for 48 hours and then autoclaved for 1 hour at 105° C. After autoclaving, the samples are dialyzed against PBS at pH 7.4 and sterile filtrated. All samples are freezer stored until use.

Example 4
Antibodies Targeted to Chloroquine that are Raised Against ADP

Antibodies against chloroquine are raised using 2-amino-5-di-ethylaminopentane (ADP), the moiety obtained on removal of the 7-chloro-quinoline moiety from the chloroquine molecule. ADP can be purchased from Sigma Chemical Co. (A48806; St. Louis, Mo.).

Example 5
Glutaraldehyde Coupling

Protein (1 mg/ml) diluted in PBS pH 7.4, was mixed with a 1:5 molar ratio of the antigen, also diluted in PBS pH 7.4. The mixture was placed on ice. Glutaraldehyde (0.2%) in PBS was then added in the same volume as the antigen plus carrier. The glutaraldehyde solution was added slowly over approximately a 10 minute period while stirring carefully. The reaction mixture was then incubated in darkness at 4° C. on an end-over-end rotator. Following incubation, the mixture was dialyzed against 1 liter PBS at 4° C. three times for a minimum of four hours each time.

Example 6
Vaccine Production for Intraperitoneal Immunization of Mice

The volume of one immunization-dosage of vaccine for intraperitoneal injection was 0.5 ml per mouse. A concentration of 50 $\mu$g/ml of the carrier molecule (25 $\mu$g per immunization) was administered. Also added to the vaccine was 0.9% NaCl (also designated RS-water); $Al(OH)_3$ (1 mg per immunization); and Merthiolate from a 1% Merthiolate solution at a final concentration in the vaccine of 0.05% Merthiolate. The vaccine was preferably produced in a 50 ml tube to enable easy removal for injection.

The molecule was mixed with the appropriate volume of 0.9% NaCl. The molecule solution was then slowly added to the $Al(OH)_3$ while shaking. Merthiolate was then added and the vaccine was again shaken. The vaccine can be stored at 4° C. until use.

Example 7
Producing Antibodies by Immunization with Conjugates of ADP Coupled to Charge-modified Protein Molecules Eight groups of 5 female CF1XbalbC mice were pre-immunized with BCG vaccine 4 weeks prior to administration of the carrier coupled ADP. Following the pre-immunization period, 0.5 ml of vaccine containing $Al(OH)_3$ adjuvant and 25 $\mu$g SP/ADP (see table 1) was administered intraperitoneally every fourteen days. The mice were bled 10 days after each immunization.

ADP was coupled to SP in accordance with Example 5. After dialyzing the mixture, the product was lyophilized. The SP-ADP coupling product was then split into three portions.

The first portion was retained for vaccine production in mouse group 1179.

The second portion was charge modified, according to Example 2, to carry a net positive charge. The mixture was lyophilized and re-dissolved in a 0.9% NaCl solution. This portion was then used for vaccine production in mouse groups 1172 and 1174–1176.

The third portion was charged modified, according to Example 3, to carry a net negative charge. This portion was then used for vaccine production in mouse groups 1173–1176.

All groups of mice, except group 1177, were immunized with equal quantities of SP (25 µg/immunization).

Group 1177 was immunized with an amount of ADP equal to the quantity present in the vaccines used for group 1172–1176 and 1179.

Table 1 Provides the dosing regimes

TABLE 1

| Group | Antigen | Abbreviated identifier |
|---|---|---|
| 1172 | ADP/SP (methylated) | ADP/SP + |
| 1173 | ADP/SP (formaldehyde treated) | ADP/SP − |
| 1174 | ADP/SP (methylated and formaldehyde treated mixture 2:1) | ADP/SP + > − |
| 1175 | ADP/SP (methylated and formaldehyde treated equal ratio (1:1)) | ADP/SP + = − |
| 1176 | ADP/SP (methylated and formaldehyde treated mixture 1:2) | ADP/SP + < − |
| 1177 | ADP (unconjugated, control) | ADP |
| 1178 | SP untreated (control) | SP |
| 1179 | ADP/SP untreated (control, comparison group) | ADP/SP |

Bleeds from the five mice in each immunization group were pooled and tested in accordance with example 8.

The control bleed was taken before the first immunization was administered and ensures that the mice do not naturally produce antibodies that cross-react with ADP.

Example 8

Testing Bleeds from Mice for Antibodies Raised Against ADP

ADP was coupled to Ovalbumin (OA) as described in Example 5. Ninety-six well high binding ELISA plates were coated with 100 µl of 2.5 µg/ml OA-ADP in 0.1 M carbonate buffer pH 9.6, and the plates were incubated overnight at 4° C. Following the incubation, the plates were washed three times in a standard ELISA washing buffer pH 7.4.

Individual bleeds (control, $1^{st}$, $2^{nd}$, $3^{rd}$ and $4^{th}$) from each group of mice were pooled, diluted and titrated in a standard dilution buffer containing bovine serum albumin and detergent. A pool of 3rd bleed plasma from all 40 mice was used as a standard and was also titrated. Volume in each well was 100 µl and the plates were incubated for 1 hour at laboratory temperature while being agitating. Following the incubation, the plates were washed 3 times in a standard ELISA washing buffer pH 7.4. Horse Radish Peroxidase conjugated rabbit anti mouse antibody (100 µl/well; P260, DAKO, Denmark) diluted 1:1000 in standard dilution buffer was then added and the plates were incubated for 1 hour at laboratory temperature while being agitated. Following the incubation, the plates were washed again three times in a standard ELISA washing buffer pH 7.4. The plates were the subjected to another wash with 0.05% citrate buffer pH 5.0. Substrate buffer (100 µl/well containing 0.05% citrate buffer with 0.4 mg/ml ortho-phenylene diamine(ODP) and 0.4 µl/ml of a 30% $H_2O_2$ solution) was added and the plates were incubated for 30 minutes in the dark. Sulphuric acid (150 µl, 1 M) was added to each well and the absorbance at 450 nm was measured.

The concentration of anti ADP antibodies in the standard pool of mouse plasma was set to be 100 Arbitrary Units (AU) and the relative concentration of each pool of mice bleed was calculated from the standard curve of this standard pool.

Example 9

Humanization of Antibodies

Obtaining Mouse IgG1 cDNA

To produce humanized mouse IgG1, the cDNA of the variable domain of the mouse IgG1 is obtained. The sequence corresponding to the Fab region is also collected to enable E. coli expression as an affinity control in the production of the humanized IgG1.

To clone IgG1, mRNA is first purified from the hybridoma cell expressing the IgG of interest. A cDNA is then produced via reverse transcription-polymerase chain reaction (RT-PCR) using a primer specific to a 3' region and the mRNA as a template. The resulting cDNA is then used as a template for a PCR reaction selecting the correct DNA sequence. Since the N-terminal region of IgG1 is variable, it is difficult to design a functional 5' primer. However, this difficulty can be overcome for the majority of IgGs by using a set of degenerative 5' primers that anneal to greater than 90% of IgG leader sequences. Generation of the 3' primer is less difficult as this sequence is typically known. In a preferred embodiment the 3' primer is specific to the J region of the heavy chain and the C-terminal region of the light chain. The PCR primers also contain restriction sites enabling insertion into the cloning vector.

The resulting PCR products are then purified and cleaved with restriction enzymes. This product is then ligated into a cloning vector such as pBluescript that has been cleaved with the same restriction enzymes. The ligated plasmid containing PCR products is then transformed into cells such as XL-blue cells and plates on B-agar plated containing 200 mg/ml ampicillin, IPTG and X-gal. Five to ten white colonies are then selected and the insert size is examined. Clones, preferably 4, containing the correct sized insert are than selected. Plasmids are purified from 10 ml cultures and the DNA is sequenced. Once the DNA has been sequenced, primers can be designed allowing the insertion of the desired DNA sequences (heavy and light) into expression vectors.

E. coli Expression

E. coli expression of proteins, is much quicker and simpler compared to the mammalian systems and allows the production of mg levels of protein in days. There are however, a number of limitations. Firstly the proteins that are produced are not necessarily folded with the correct disulphide linkages and may simply be produced as aggregated protein and have to be refolded. There are however, systems that allow the proteins to be secreted into the periplasm, an environment that is more conducive to the formation of disulphide linkages. This system has been successfully used previously for the production of Fab fragments. A second drawback of using E. coli is that it does not glycosylate the protein produced. This is a major reason why it is not thought feasible to use this system for the expression of IgG1. However, E. coli expression is a good way to produce Fab fragments that can be used to verify the affinity of the humanized IgG1.

Primers are designed to allow the insertion the DNA sequence coding for both the heavy and light Fab chains into a modified pGH433laci expression vector. A enterotoxin II signal sequence (stIIss) will be introduced to the N-terminal of the insert to direct secretion of the Fab into the periplasmic space of the E. coli. A Hexa His binding sequence will also be added to the C-terminal of the heavy chain allowing binding and purification on a Nickel chelating -NTA. The resulting PCR product will be cloned, purified and sequenced as previously described for the cloning vector. The resulting pMHL (mouse heavy and light chain) vector are then transformed into BL21 cells.

The transformed cells are grown in LB media (shaking flasks). Fab fragment expression is induced using IPTG. After 2–4 hours the cells are collected and the Fab fragments are isolated and purified on a Ni-NTA column. The production of Fab fragments in *E. coli* provides a useful technique to produce special multimeric labeled fusion Fabs for use in diagnosis.

Cloning Human IgG1

Unlike cloning of the mouse Fab, for human the entire IgG heavy constant region must be cloned. However, since the variable region human IgG is not of interest, both the 3' and 5' primers can be designed from known sequences. The primers also contain restriction sites allowing insertion into a cloning vector. The IgG1 heavy and light chain coding sequences are cloned from a commercially available human spleen cell cDNA library into a cloning vector such as the pBluescript cloning vectors. Verification is performed as described above for the mouse.

Chimerized Fab

Once the coding sequence for the human and mouse have been determined, primers are designed to select for the mouse variable and human constant regions. The primers contain an annealing sequence that allows the two fragments to anneal together and act as templates for a further PCR reaction. The final primers contain the stllss sequence and restriction sites to enable the insertion of the coding sequence into an expression vector such as pET3a. After cloning and sequence, the chimeric Fab is expressed and its affinity is compared to that of the mouse Fab.

Humanized Fab

Since there are also considerable differences in framework regions of the variable domain which can result in a chimeric Fab having less affinity than the mouse Fab, in a preferred embodiment, the general framework of the mouse variable region of the chimeric Fab is mutated to enhance affinity. The general framework of the intact mouse variable region is compared with the known human sequences. There are around 1,200 heavy and 1,200 light chain sequences deposited in the Kabat database. Using known structures and up to date modeling programs, specific residues or sequences of the framework region are mutated. The effect of these mutations on the Fab affinity is then compared to affinities of the mouse and chimeric Fabs.

Cloning Humanized IgG1 in CHO Cells

A two-stage PCR procedure similar to that used to form the chimeric Fab is used to create the complete humanized IgG1 heavy and light chain inserts for the expression plasmid. The expression plasmid is then cloned in *E. coli*, purified and verified as discussed above.

Due to the expectedly large amounts of humanized antibody required, it is preferred that CHO cells in suspension (CHO-S) be used as the expression system. More preferred is use of CHO-S cells that are especially adapted to serum free media so that purification of IgG for clinical use is simplified.

The CHO-S cells are transformed with two expression vectors, one containing the light chain of IgG1 and the other containing the heavy chain of IgG1. Selection for transformed cells and gene amplification is preferably carried out using the neomycin (G-418 system).

CHO-S cells are preferably transformed using the DMRIE-C system (Gibco-BRL) which does not require the cells to be in serum containing media. The cells are then incubated for 48 hours before being seeded into a 125 ml shake flask in 35 ml of CD CHO Medium containing 300 $\mu$M G-418 at a cell density of 3–5×10$^5$ cells/ml. Cells are allowed to reach a density of 2×10$^6$ cells/ml. Subculture of the cell suspension is continued every 3 to 5 days for 2 to 3 weeks. At this point the concentration of G-418 is increased to 500 for another 2 to 3 weeks. After selection, the cells are plated into 96 well plates at a concentration of 0.5–1 cells/well. After 2 to 3 weeks the media is tested by ELISA and SDS-PAGE for the presence of IgG1. The five highest clones are then subcultured as described above in media containing 500 $\mu$M G-418. The IgG1 expression level in the media is then examined by ELISA and SDS-PAGE and the highest, most pure, IgG expressing subculture is selected.

What is claimed is:

1. A method for producing antibodies against molecules in a host animal comprising:

(a) producing a modified carrier protein from unmodified carrier protein wherein the first portion of said unmodified carrier protein is chemically modified to carry a net positive charge and the second portion is chemically modified to carry a net negative charge;

(b) coupling a molecule to said modified carrier proteins obtained in step (a) to form a complex;

(c) forming a balanced charge mixture comprising complexes obtained in step (b);

(d) pre-immunizing a host animal with an unmodified carrier protein;

(e) administering to the host animal the balanced charge mixture obtained in step (c) so that antibodies are produced against the molecule; and (f) isolating the antibodies or B cells producing antibodies against the molecule from the host animal.

2. The method of claim 1 further comprising humanizing the antibody isolated from the host animal.

3. The method of claim 1 wherein the molecule is a hapten or other B cell antigen.

* * * * *